United States Patent [19]

Nelson

[11] Patent Number: 4,810,425
[45] Date of Patent: Mar. 7, 1989

[54] PREPARATION OF PHOSPHINIC ACIDS

[75] Inventor: Gunner E. Nelson, Baton Rouge, La.

[73] Assignee: Ethyl Corporation, Richmond, Va.

[21] Appl. No.: 165,082

[22] Filed: Mar. 7, 1988

[51] Int. Cl.$^4$ .............................. C07F 9/30; C07F 9/34
[52] U.S. Cl. .......................... 260/502.4 R; 260/543 P
[58] Field of Search ...................... 260/502.4 R, 543 P

[56] References Cited

U.S. PATENT DOCUMENTS

| 3,036,132 | 5/1962 | Becker | 260/606.5 |
| 3,098,865 | 7/1963 | Schimmelschmidt et al. | 260/502.4 R |
| 3,149,137 | 9/1964 | Huffman et al. | 260/448 |
| 3,579,576 | 5/1971 | Angstadt | 260/502.4 R |
| 3,584,043 | 6/1971 | Maier | 260/502.4 R |

OTHER PUBLICATIONS

Dickson et al., *Australian Journal of Chemistry*, (1962) p. 711, et. seq.
Oklobystin et al., *Academy of Sciences, U.S.S.R.*, (1958), pp. 977–979 (Eng. trans.).

Primary Examiner—J. E. Evans
Attorney, Agent, or Firm—John F. Sieberth

[57] ABSTRACT

A process for the preparation of a phosphinic acid,

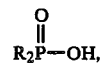

said process comprising reacting a phosphorus oxyhalide, $POX_3$, with an alkali metal tetraalkyl aluminate, $MAlR_4$, wherein X is halogen, M is an alkali metal, and R is an alkyl radical.

10 Claims, No Drawings

PREPARATION OF PHOSPHINIC ACIDS

FIELD OF THE INVENTION

This invention pertains to alkylating phosphorus oxyhalides ($POX_3$, where X=halogen). It also pertains to use of alkali metal tetraalkyl aluminates ($MAlR_4$) as alkylating agents, and to preparation of phosphinic acids

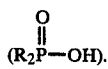

DESCRIPTION OF RELATED ART

U.S. Pat. No. 3,149,137 discloses inter alia reaction of trialkylaluminums with phosphorus oxyhalides to produce monoalkylphosphonyl dihalides.

Dickson et al, *Australian Journal of Chemistry*, (1962) Page 711 et. seg. discusses reaction of $MAlR_4$ compounds with some halides of Group IV and VB elements.

Okhlobystin et al, *Academy of Sciences, U.S.S.R.*, (1958), pages 977–979 (Eng. trans.) discusses the reaction of $PCl_3$ and trialkylaluminums.

U.S. Pat. No. 3,036,132 discloses the reaction of $(MAlR_4)_n$ compounds with $PX_3$ wherein X is chlorine or bromine.

SUMMARY OF THE INVENTION

A phosphinic acid is produced by reacting an alkali metal tetraalkyl aluminate with a phosphorus oxyhalide. The phosphinic acids are useful as chemical intermediates.

DESCRIPTION OF PREFERRED EMBODIMENTS

This invention comprises a process for the preparation of a phosphinic acid,

said process comprising reacting a phosphorus oxyhalide, $POX_3$, with an alkali metal tetraalkyl aluminate $MAlR_4$, wherein X is halogen, M is an alkali metal, and R is an alkyl radical.

The phosphorus oxyhalide ($POX_3$) used as a reactant in this invention is preferably selected from compounds in which X is chlorine or bromine. Preferably, each radical depicted by X is the same. Phosphorus oxychloride, $POCl_3$, is a preferred reactant.

The alkylating agent used in this invention is a metal tetrahydrocarbyl aluminate. Alkali metal compounds having the formula $MAlR_4$ are preferred. The sodium compounds are highly preferred. Each radical depicted by R is preferably an alkyl radical. The radicals may be alike or different; preferably they are the same. There is no real size limitation for the radicals. The preferred size range is obtained by such secondary characteristics as availability, cost, etc. Preferably the reactants have less than 20 carbon atoms; most preferably they have from one to about 14 carbon atoms. Highly preferred radicals have 6 to 12 carbons. Because of their availability it is preferred that the radicals be straight chain alkyls such as methyl, ethyl, n-propyl, n-butyl, n-hexyl, n-octyl, n-decyl, n-dodecyl, tetradecyl, and the like.

The reactants are combined in a mole ratio of about 1 to 1, i.e. an equimolar ratio can be used, as well as a slight excess of either reactant.

The process is preferably carried out in the presence of an inert liquid reaction medium such as petroleum ether, or other paraffinic material such as hexane or octane.

The process is conducted at a temperature which gives a suitable reaction rate, but which is not so high as to cause formation of an undesirably large amount of unwanted by-products. The exact temperature selected is not critical, but is dependent at least to some extent on the reactivity of the reactants employed. Generally, temperatures from ambient to about 60° C. are used; however, temperatures somewhat outside this range can be employed, if desired. In many instances the reaction is exothermic, and is controlled by such means as the rate of addition of one reactant to the other, and/or by an external ice bath.

The reaction proceeds well at atmospheric pressure; higher and lower pressures can be used if desired.

The reaction time is not a truly independent variable but is dependent at least to some extent on the other reaction conditions employed. Thus, for example, it depends to some extent on the reactivity of the reactants and/or the process temperature. The reaction is usually complete in 24 hours or less. Preferred reaction times are 1 to 10 hours.

EXAMPLE 1

A solution (63.2 grams) containing 56.2 millimoles of sodium tetrahexyl aluminate in n-hexane was diluted with 25 milliliters of petroleum ether. To this mixture was added 8.59 grams (56 millimoles) of $POCl_3$. The addition was conducted over a 1.5 hour period. Periodic cooling with an ice bath was required to maintain a temperature between ambient and 50° C. After addition was complete, the resultant mixture was stirred overnight at room temperature.

The mixture was then hydrolyzed using 10 percent sodium hydroxide. After hydrolysis, the organic phase was separated and extracted with 6N HCl until clear. Thereafter, the organic layer was dried over magnesium sulfate and then evaporated to remove solvent, leaving a residue weighing 29.2 grams. The residue was analyzed by gas liquid chromatography versus an internal standard. Analysis indicated a 10.8 percent yield of trihexyl phosphine oxide. Thereafter, the fluid was triturated with acetone resulting in the precipitation of 5.7 grams of solids which were presumed to be a mixture of organic phosphorus acids.

EXAMPLE 2

The reaction in the above example was essentially repeated using 60.6 millimoles of each reactant. After reaction was complete, solvent was removed under reduced pressure. Thereafter, the mixture was hydrolyzed with 3N HCl. After hydrolysis, the product mixture was washed three times with 100 milliliter portions of 3N HCl, and the organic phase was then washed three times with 5 percent sodium hydroxide. The aqueous extracts were combined and acidified yielding, after filtration and drying, 4.56 grams of acid (19.5 millimoles).

A 1 gram portion of the dry acid was treated with 3 milliliters of thionyl chloride, and heated at 50° C. for 1 hour. After heating, excess thionyl chloride was removed under vacuum. Then, 1 milliliter of pyridine in 50 milliliters of dibutylether was added. To this mixture was added 5 milliliters of anhydrous ethyl alcohol. The product solution was washed with water, and then with dilute hydrochloric acid.

Gas liquid chromatographic analysis showed a single peak. Also, $^{31}P$ NMR showed a single peak at −58 ppm relative to $H_3PO_4$. A sample of recrystallized acid gave a melting point of 79°–80° C. These analytical indicia are consistent with dihexyl phosphinic acid;

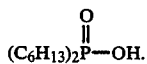

EXAMPLE 3

To 10.5 grams (68 millimoles) of $POCl_3$ and 20 milliliters of octane was added 73 millimoles of sodium tetraoctyl aluminate. During the addition, the temperature was maintained at or about 60° C. by controlling the addition rate. When addition was complete, the mixture was heated for 1.5 hours at 110° C. After cooling, the resultant reaction mixture was hydrolyzed with 50 milliliters of 3N HCl. The organic phase was separated, washed with 50 milliliters of 3N HCl and then three times with 50 milliliters water. After washing, the resultant organic layer was dried over magnesium sulfate.

The dry solution was evaporated under vacuum to yield 20.3 grams of a white, waxy solid which was recrystallized from 60 milliliters of hexane to yield 12.8 grams of dioctyl phosphinic acid;

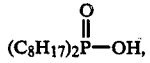

melting point 84°–6° C. (64.8 percent yield).

The procedure of the above examples can be repeated using phosphorus oxybromide in place of the phosphorus oxychloride. Similar results are obtained.

The process of the above examples can be repeated using sodium tetraalkyl aluminates wherein the alkyl reactants are selected from methyl, ethyl, butyl, decyl, dodecyl, and tetradecyl. Such processes can be conducted at a temperature of from ambient to about 60° C., and at atmospheric pressure. These processes can be conducted using a ratio of the alkyl aluminate to the oxyhalide of 1 to 1; alternatively, a slight excess of either reactant can be employed.

In light of the above detailed description of this invention, a skilled practitioner can make many substitutions or alterations without departing from the spirit or scope of the appended claims.

I claim:

1. Process for the preparation of a phosphinic acid,

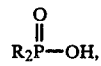

said process comprising reacting a phosphorus oxyhalide $POX_3$, with an alkali metal tetraalkyl aluminate, $MAlR_4$, wherein X is halogen, M is an alkali metal, and R is an alkyl radical.

2. The process of claim 1, wherein said phosphorus oxyhalide is phosphorus oxychloride, $POCl_3$.

3. The process of claim 1, wherein said alkali metal tetraalkyl aluminate is a sodium aluminate, $NaAlR_4$.

4. The process of claim 2, wherein said alkali metal tetraalkyl aluminate is a sodium aluminate, $NaAlR_4$.

5. The process of claim 3, wherein each radical depicted by R is the same, and has from about 1 to about 12 carbon atoms.

6. The process of claim 1, wherein the molar ratio of said oxyhalide and said tetraalkyl aluminate is about 1:1.

7. The process of claim 1, wherein said phosphinic acid is

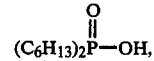

said oxyhalide is $POCl_3$, and said aluminate is $NaAl(C_6H_{13})_4$.

8. The process of claim 1, wherein said phosphinic acid is

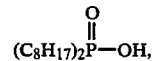

said oxyhalide is $POCl_3$, and said aluminate is $NaAl(C_8H_{17})_4$.

9. A process for the preparation of dihexyl phosphinic acid, said process comprising reacting a substantially equimolar mixture of sodium tetrachexyl aluminate and phosphorus oxychloride, and hydrolyzing the reaction mixture thereby produced, whereby said acid product is formed.

10. A process for the preparation of dioctyl phosphinic acid, said process comprising reacting a substantially equimolar mixture of sodium tetraoctyl aluminate and phosphorus oxychloride, and hydrolyzing the reaction mixture thereby produced, whereby said acid product is formed.

* * * * *